(12) United States Patent
Sawyers

(10) Patent No.: US 10,107,741 B2
(45) Date of Patent: Oct. 23, 2018

(54) INPUT AND OUTPUT OPTICAL SYSTEMS FOR MULTIPASS SPECTROSCOPIC ABSORPTION CELLS

(71) Applicant: Duvas Technologies Limited, London (GB)

(72) Inventor: Craig Sawyers, Oxford (GB)

(73) Assignee: DUVAS TECHNOLOGIES LIMITED, London (GB)

(*) Notice: Subject to any disclaimer, the term of this patent is extended or adjusted under 35 U.S.C. 154(b) by 0 days.

(21) Appl. No.: 15/287,011

(22) Filed: Oct. 6, 2016

(65) Prior Publication Data

US 2017/0102315 A1 Apr. 13, 2017

Related U.S. Application Data

(60) Provisional application No. 62/238,537, filed on Oct. 7, 2015.

(51) Int. Cl.
| | |
|---|---|
| *G01N 21/03* | (2006.01) |
| *G01N 21/3504* | (2014.01) |
| *G01N 21/33* | (2006.01) |
| *G01J 3/02* | (2006.01) |
| *G01J 3/10* | (2006.01) |
| *G01J 3/42* | (2006.01) |

(52) U.S. Cl.
CPC .......... *G01N 21/031* (2013.01); *G01J 3/027* (2013.01); *G01J 3/0264* (2013.01); *G01J 3/108* (2013.01); *G01J 3/42* (2013.01); *G01N 21/33* (2013.01); *G01N 21/3504* (2013.01); *G01N 2201/0231* (2013.01); *G01N 2201/0627* (2013.01); *G01N 2201/12* (2013.01)

(58) Field of Classification Search
CPC .......... G01J 3/0264; G01J 3/027; G01J 3/108; G01J 3/42; G01N 21/031; G01N 21/33; G01N 21/3504; G01N 2201/0231; G01N 2201/0627; G01N 2201/12
See application file for complete search history.

(56) References Cited

U.S. PATENT DOCUMENTS

| | | | | |
|---|---|---|---|---|
| 3,730,629 A | * | 5/1973 | Rentzepis | ............ G01J 3/2889 356/300 |
| 5,739,537 A | * | 4/1998 | Siesler | ................ G01N 21/552 250/339.11 |

(Continued)

*Primary Examiner* — Marcus Taningco
(74) *Attorney, Agent, or Firm* — Christopher J. McKenna; Foley & Lardner LLP

(57) ABSTRACT

Systems and methods of the present disclosure are directed to detecting species within a fluid using a multi-pass absorption cell and a spectrometer. The absorption cell includes a plurality of mirrors arranged in a manner such that a detection light traverses multiple passes through the fluid within the absorption cell. In some implementations, the detection light is reflected by the plurality of mirrors to form optical paths in more than one plane. The system also includes an electronic unit configured to receive and process spectral data from the spectrometer. In some implementations, the electronic unit communicates with at least one computational unit over a communication interface to send a portion of the spectral data for processing. The electronic unit may also receive processed data from the computational unit.

8 Claims, 16 Drawing Sheets

(56) References Cited

U.S. PATENT DOCUMENTS

| | | | | |
|---|---|---|---|---|
| 6,108,083 A | * | 8/2000 | Machler | G01J 3/02 |
| | | | | 356/246 |
| 2003/0193662 A1 | * | 10/2003 | DiFoggio | E21B 47/102 |
| | | | | 356/128 |
| 2006/0290934 A1 | * | 12/2006 | Boekelman | G01N 21/031 |
| | | | | 356/432 |
| 2015/0260695 A1 | * | 9/2015 | Spartz | G01N 30/74 |
| | | | | 250/339.01 |

* cited by examiner

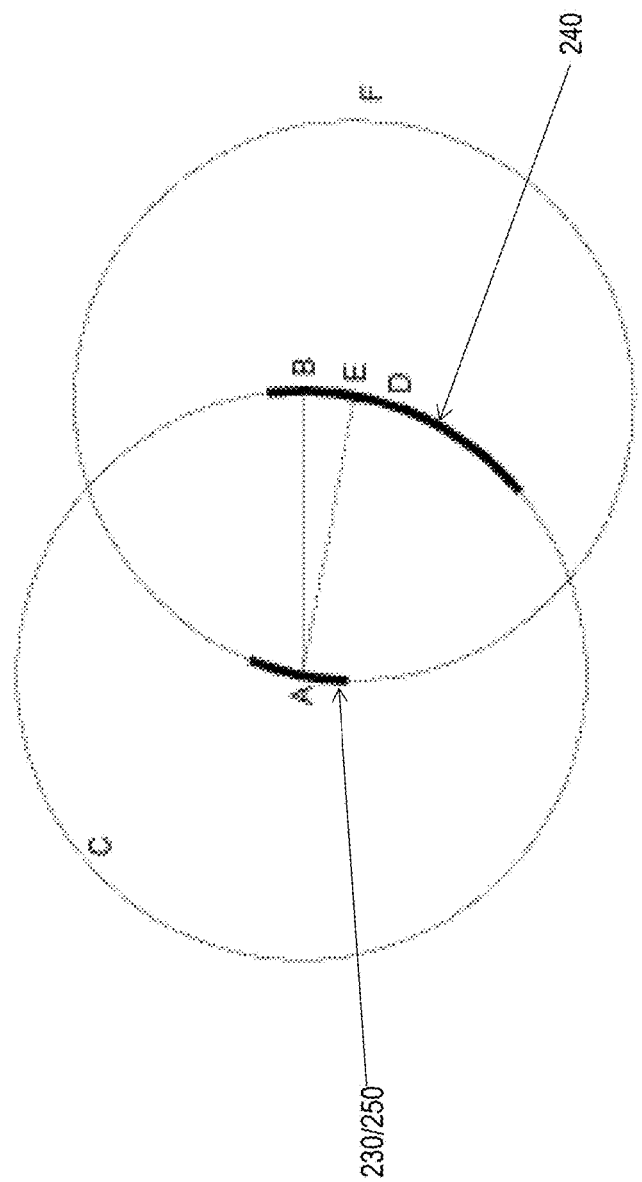

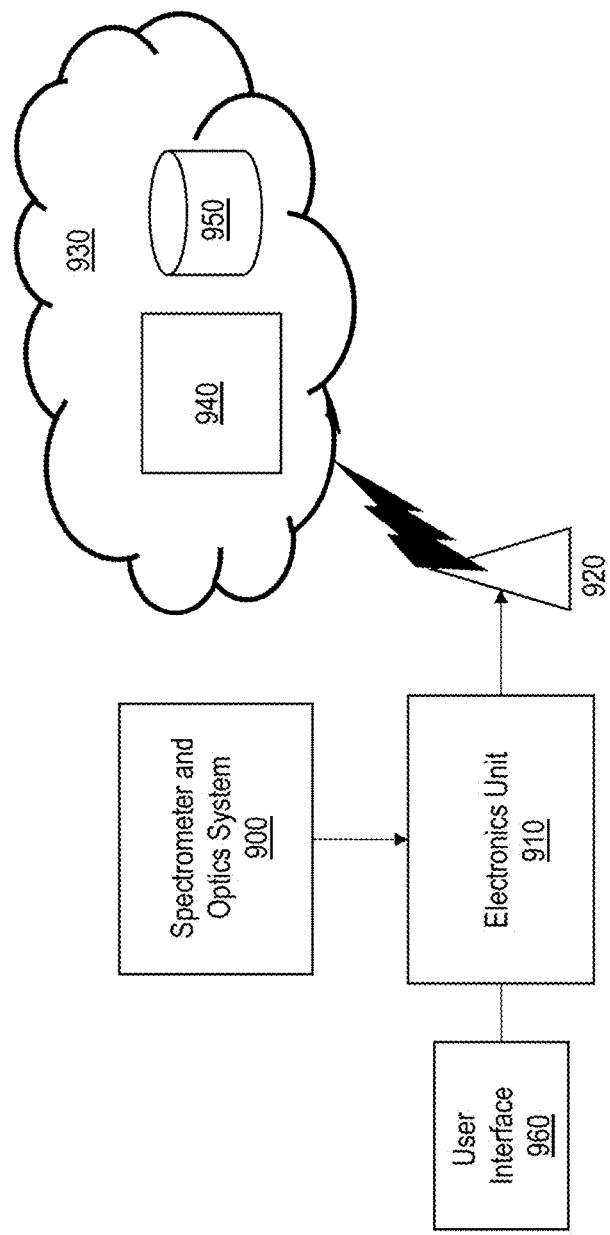

INPUT AND OUTPUT OPTICAL SYSTEMS FOR MULTIPASS SPECTROSCOPIC ABSORPTION CELLS

CROSS-REFERENCE TO RELATED APPLICATIONS

The present application for patent claims priority to U.S. Provisional Application No. 62/238,537 entitled "DESIGN OF INPUT AND OUTPUT OPTICAL SYSTEMS FOR MULTIPASS SPECTROSCOPIC ABSORPTION CELLS," filed Oct. 7, 2015, which is incorporated herein in its entirety.

FIELD OF THE DISCLOSURE

The present disclosure is generally directed to spectroscopy. In particular, the present disclosure describes techniques for detecting gas and vapor species using a multi-pass absorption cell.

BACKGROUND OF THE DISCLOSURE

Optical spectrometers measure the presence or absence of light at various wavelengths, and when combined with a known light source, can be used to identify various species of gas or liquid by observing which wavelengths are absorbed. Each species of gas or liquid has a unique spectral absorption characteristics and therefore can be uniquely identified by its absorption signature.

BRIEF SUMMARY OF THE DISCLOSURE

In one aspect a system for the identification of species in gas or liquid includes a light source, an input coupling optical unit, which couples the light into a multi-pass optical cell, and optical coupling optical unit, which couples the light exiting the optical cell to a spectrometer and an electronic unit that analyzes the data coming from the spectrometer where the light source and the spectrometer are positioned at opposite ends of the optical cell. The input optical coupling unit includes an air-spaced achromatic doublet lens and a prismatic periscope. The output optical coupling unit includes fused silica prism, fused silica lenses and an off axis parabolic mirror. The temperature of the system is controlled such that condensation from moisture in the environment is minimized.

In another aspect, a light source includes a plurality of LEDs (or lasers) each with a slightly different wavelength, and a spectrometer, which detects the light emitted from the light source after it passes through a sample of material. In the light source and the spectrometer, the plurality of LEDs is constructed using individual ultra violet LEDs. In the light source and the spectrometer, the plurality of LEDs is constructed using ultra violet LEDs fabricated on the same die. In the light source and the spectrometer, the plurality of LEDs is constructed using individual infrared LEDs. In the light source and the spectrometer, the plurality of LEDs is constructed using infrared LEDs fabricated on the same die.

In another aspect, a light source includes a plurality of LEDs, a fluorescer, and a spectrometer which detects the light emitted from the light source after it passes through a sample of material. In the light source and the spectrometer, the plurality of LEDs is constructed using individual ultra violet LEDs. In the light source and the spectrometer, the plurality of LEDs is constructed using ultra violet LEDs fabricated on the same die. In the light source and the spectrometer, the plurality of LEDs is constructed using individual infrared LEDs. In the light source and the spectrometer, the plurality of LEDs is constructed using infrared LEDs fabricated on the same die.

In another aspect, a light source includes a single LED, a fluorescer, and a spectrometer, which detects the light emitted from the light source after it passes through a sample of material. In the light source and the spectrometer, the LED emits ultra violet light. In the light source and the spectrometer, the LED emits infra-red light.

In another aspect, an apparatus includes a multi-pass optical cell where the optical paths are defined by the reflections of a plurality of mirrors configured such that the optical paths lie in a plurality of planes. In the multi-pass optical cell, the optical paths are arranged such that there is no clipping of the input or output light beams on any of the plurality of mirrors. In the multi-pass optical cell, the position of the plurality of mirrors can be adjusted by a plurality of electrically stimulated actuators. In the multi-pass optical cell, the shape of the plurality of mirrors can be altered by a plurality of electrically stimulated actuators. In the multi-pass optical cell, one or a plurality of mirrors are non-circular in shape. In the multi-pass optical cell, the position of the plurality of mirrors can be adjusted by a plurality of electrically stimulated actuators and one or a plurality of mirrors are non-circular in shape. In the multi-pass optical cell, the shape of the plurality of mirrors can be altered by a plurality of electrically stimulated actuators and one or a plurality of mirrors are non-circular in shape. In the multi-pass optical cell, the metal parts have a fluorocarbon coating.

In another aspect, a system for the identification of species in gas or liquid, includes a light source, a spectrometer and a local electronic unit that analyzes the data coming from the spectrometer where the electronic unit is in communications with a plurality of other computational and storage units commonly referred to as the cloud. In the system, at least part of the communications mechanism is wireless. In the system, analysis of the spectrometer data is done partially on the local electronic unit and partially in the cloud. In the system, additional species identification information can be transferred from the cloud to the local electronics unit to alter the local species identification capabilities of the local electronics unit.

In another aspect, a system for identifying species in a fluid includes a light source generating a detection light, an input optical coupling unit configured to receive the detection light at a first angle and output the detection light at a second angle, a multi-pass absorption cell containing the fluid having an input port positioned at one end of the cell and an output port positioned at an opposing end of the cell, the cell configured to receive the detection light output by the input optical coupling at the input port, pass the detection light through the fluid, and output the detection light through the output port; an output optical coupling unit configured to receive the detection light output by the cell at a third angle and output the detection light at a fourth angle; a spectrometer configured to receive the detection light output by the output optical coupling unit and generate spectral data related to the detection light; and an electronic unit configured to receive spectral data from the spectrometer and analyze the spectral data.

In some embodiments, the input optical coupling unit includes an air-spaced achromatic doublet lens and a periscope. In some embodiments, the output optical coupling unit includes a fused silica prism, a fused silica lens, and an off-axis parabolic mirror. In some embodiments, the output optical coupling unit includes a fused silica prism, a fused silica lens, and an off-axis parabolic mirror. In some embodiments, the system further includes a temperature controller for controlling the temperature of the spectrometer.

In another aspect, a system for identifying species in a fluid includes a light source including a plurality of at least one of light emitting diodes (LEDs), wherein each of the plurality of LEDs generates light at a different wavelength; and a spectrometer configured to detect the light generated by the plurality of LEDs, having passed through a fluid. In one or more embodiments, the plurality of LEDs include a plurality of ultra-violet LEDs. In one or more embodiments, the plurality of LEDs include a plurality of ultra-violet LEDs disposed on a single semiconductor die. In one or more embodiments, the plurality of LEDs include a plurality of infra-red LEDs. In one or more embodiments, the plurality of LEDs include a plurality of infra-red LEDs disposed on a single semiconductor die. In one or more embodiments, the light source further includes a fluorescence agent.

In another aspect, a system for identifying species in a fluid includes a light source including a single light emitting diodes (LEDs) and a fluorescence agent; and a spectrometer configured to detect the light generated by the plurality of LEDs, having passed through a fluid. In one or more embodiments, the single LED is an ultra-violet LED. In one or more embodiments, the single LED is an infra-red LED.

In another aspect, a multi-pass absorption cell for containing a fluid, the cell configured to receive a detection light from a light source, includes a plurality of mirrors positioned within the cell in relative positions such that the received detection light is reflected off of each of the plurality of mirrors to form optical paths that lie in a plurality of planes. In one or more embodiments, an entire boundary of a beam of the detection light incident on any one of the plurality of mirrors is within a perimeter of the respective mirror. In one or more embodiments, the system further includes a plurality of electrically stimulated position actuators corresponding to the plurality of mirrors configured to adjust a position of at least one of the plurality of mirrors. In one or more embodiments, the system further includes a plurality of electrically stimulated position actuators corresponding to the plurality of mirrors configured to adjust a shape of at least one of the plurality of mirrors. In one or more embodiments, at least one of the plurality of mirrors is non-circular in shape. In one or more embodiments, at least one of the plurality of mirrors is non-circular in shape. In one or more embodiments, at least one of the plurality of mirrors is non-circular in shape. In one or more embodiments, the system further includes a fluorocarbon coating on at least one metal surface of the cell.

In another aspect, a system for identifying species in a fluid includes a light source generating a detection light. The system further includes a spectrometer configured to receive the detection light after the detection light has passed through the fluid, and generate spectral data related to the detection light. The system further includes an electronic unit configured to receive and process the spectroscopic data received from the spectrometer, the electronic unit including at least one communication interface to communicate with at least one computational unit and at least one storage unit. In one or more embodiments, the communication interface includes a wireless interface. In one or more embodiments, the electronic unit is configured to process a portion of the spectral data and communicate another portion of the spectral data to the at least one computational unit over the communication interface. In one or more embodiments, the electronic unit is further configured to receive from the at least one computational unit or the at least one storage unit species identification information different from species identification information present at the electronic unit.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 6D depicts mirror overlays on the example representation shown in FIG. 6C.

FIG. 9 shows a block diagram representation of an electronic unit connected to a cloud computer.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein.

Section B describes systems and methods for detecting gas and vapor species using a spectrometer and a multi-pass absorption cell.

A. Computing and Network Environment

Figure 1A:
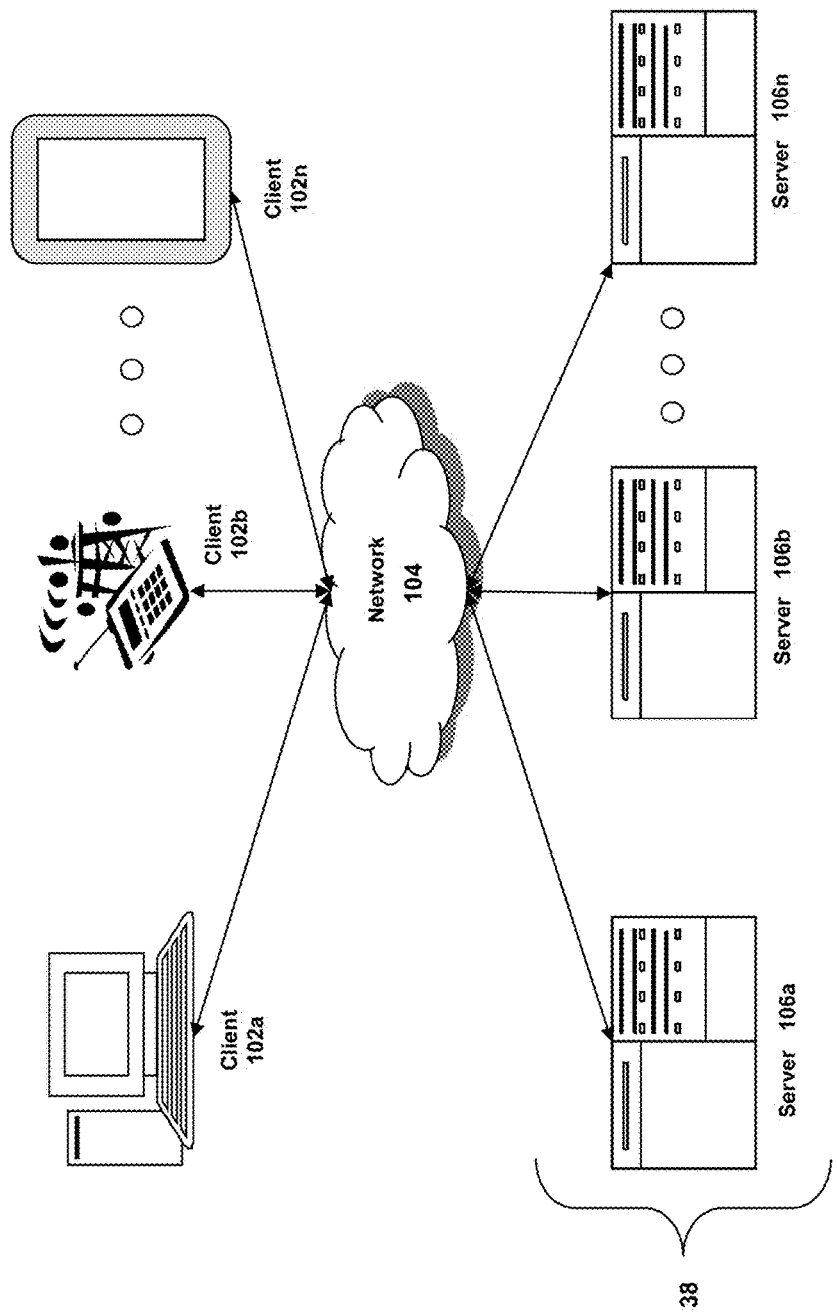
FIG. 1A is a block diagram depicting an embodiment of a network environment comprising a client device in communication with server device.

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
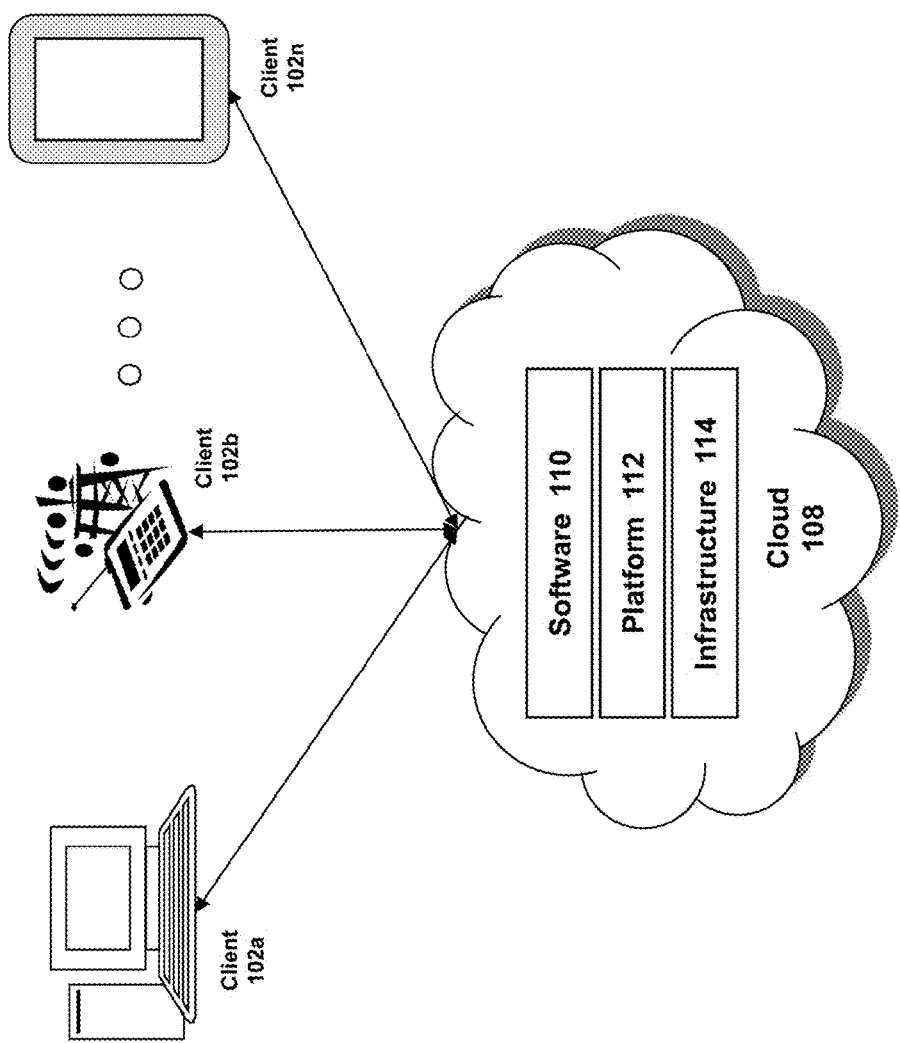
FIG. 1B is a block diagram depicting a cloud computing environment comprising client device in communication with cloud service providers.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS can include infrastructure and services (e.g., EG-32) provided by OVH HOSTING of Montreal, Quebec, Canada, AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
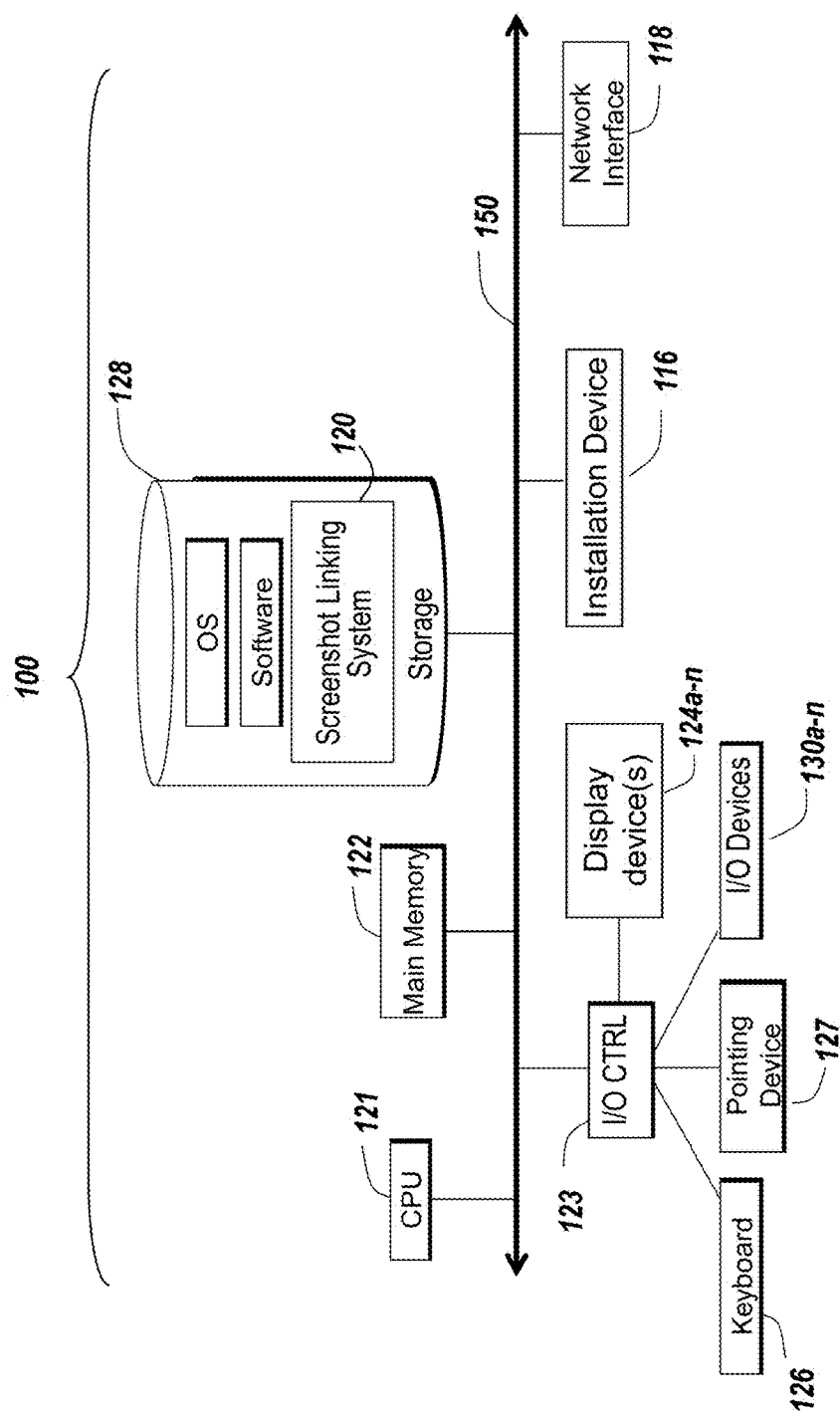
FIGS. 1C and 1D are block diagrams depicting embodiments of computing devices useful in connection with the methods and systems described herein.
Figure 1D:
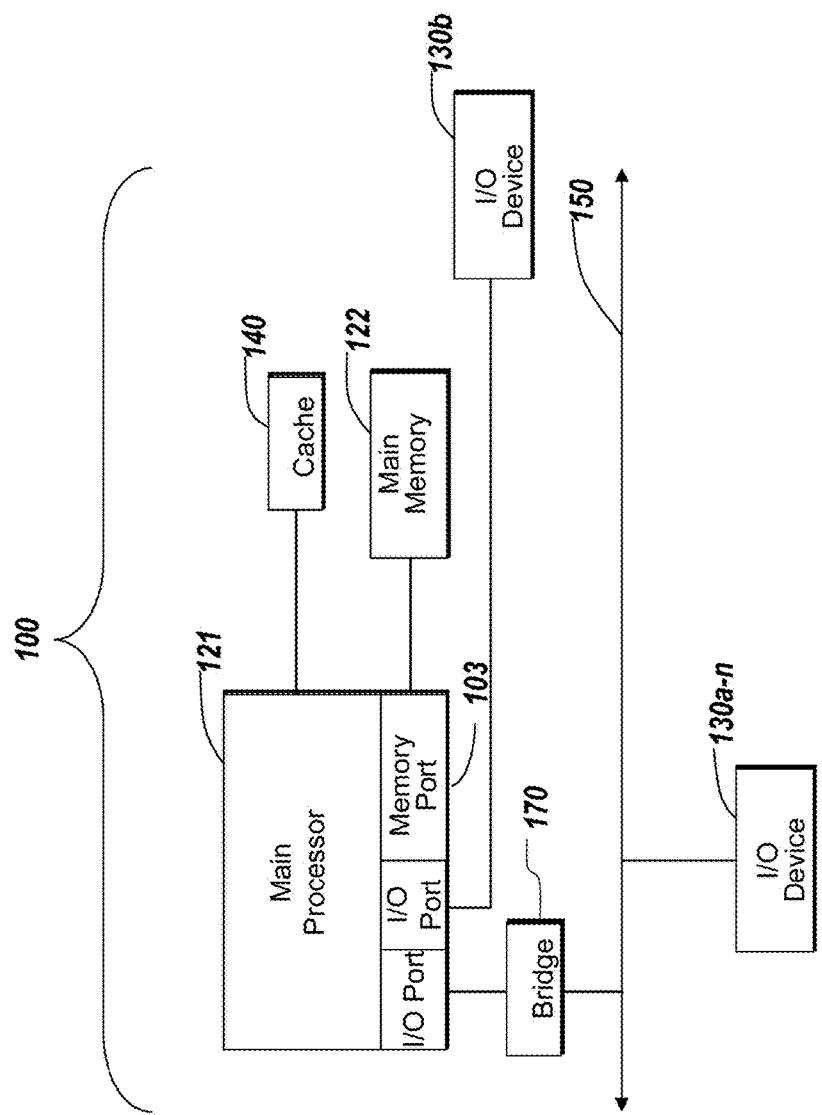

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a screenshot linking system 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WIT, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or auto stereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the screenshot linking system 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage devices 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2022, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is an eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 are monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Detecting Gas and Vapor Species Using Multi-Pass Spectroscopic Absorption Cells Optical spectrometers measure the presence or absence of light at various wavelengths, and when combined with a known light source, can be used to identify various species of gas or liquid by observing which wavelengths are absorbed. Each species of gas or liquid has a unique spectral absorption characteristics and therefore can be uniquely identified by its absorption signature. The known light source can be made to travel along a path long enough to enable it to pass through enough of the gas or liquid such that when it enters the spectrometer, the light at the specific wavelengths in the species' signature is sufficiently attenuated to allow for the signature to be detected. The higher the concentration of the gas or liquid, the more attenuation will occur. One can then also detect the small concentration level of a gas or liquid species if the spectrometer is sensitive enough. As the need for environmental monitoring of particular pollutants has increased, the use of optical spectrometers has also increased.

In one or more embodiments, ultraviolet light spectroscopy can be used to detect and quantify compounds in the environment. Often, the need for real-time and reliable quantification of certain pollutants or toxins is desirable, as, for example, in the case of pollution monitoring or an industrial accident. Additional situations include regular monitoring around power plants or refineries or near natural sources of toxic gases such as volcanoes. Portable units presently available are limited regarding their real portability, detection sensitivity, capability to simultaneously resolve multiple chemicals, the wavelength able to be measured, the ability to resolve data quickly, and reliability of calibration.

Certain gas or liquid species can impact the environment even in small concentrations. Therefore, it is desirable to design a chemical detection system that is highly sensitive. To increase gas or liquid species detection sensitivity in a system using a spectrometer, the light source usually traverses a long path from the source to the spectrometer. For high detection sensitivities, the path length can be several meters. However, it is desirable that a mobile system that provides both chemical detection and identification in the field be portable, small, and easily deployed. For detection of gases and liquids in the field, an instrument requiring longer path lengths poses several challenges. In some systems, the light source and the spectrometer are deployed separately, but then they must be aligned and calibrated, which can be a difficult process. A device consisting of mirrors can be used to bounce the light back and forth to create a longer path within a shorter distance, with the light making multiple passes such that a more manageable device that maintains its alignment can be constructed. One such embodiment of such a multi-pass apparatus is called an absorption cell. One example of an absorption cell is a White cell. A White cell consists of three parabolic mirrors precisely aligned in a particular way to create multiple unique paths, thus reducing the physical separation required between the light source and the spectrometer. Alignment is critical and must be maintained over the operating life of the unit. The need for greater portability, higher sensitivity, and more rugged detectors is driving the need to improve further the size, weight, power, and robustness and continue to make design improvements to the White cell.

The following discusses a highly portable air or liquid monitoring system or apparatus that may be based on ultraviolet, visible, and/or infrared spectroscopy or any combination thereof that may operate either in an open or closed path system. The system may relate to the detection and quantification of chemicals either in the open air environment or a sample that is inserted into a chamber. The system may function on the principle of collecting a full spectrum (large bandwidth) of data points utilizing a spectrometer and therefore may afford the capability to perform real-time multi-gas analysis. Embodiments discussed below allow a decrease in the overall size and weight of the monitoring system and improves its usability and robustness. In addition, by utilizing advancements in cloud connectivity, large amounts of signature analysis information can be accessed, complex analysis can be performed, and results can be presented to operators in the field.

Figure 2:
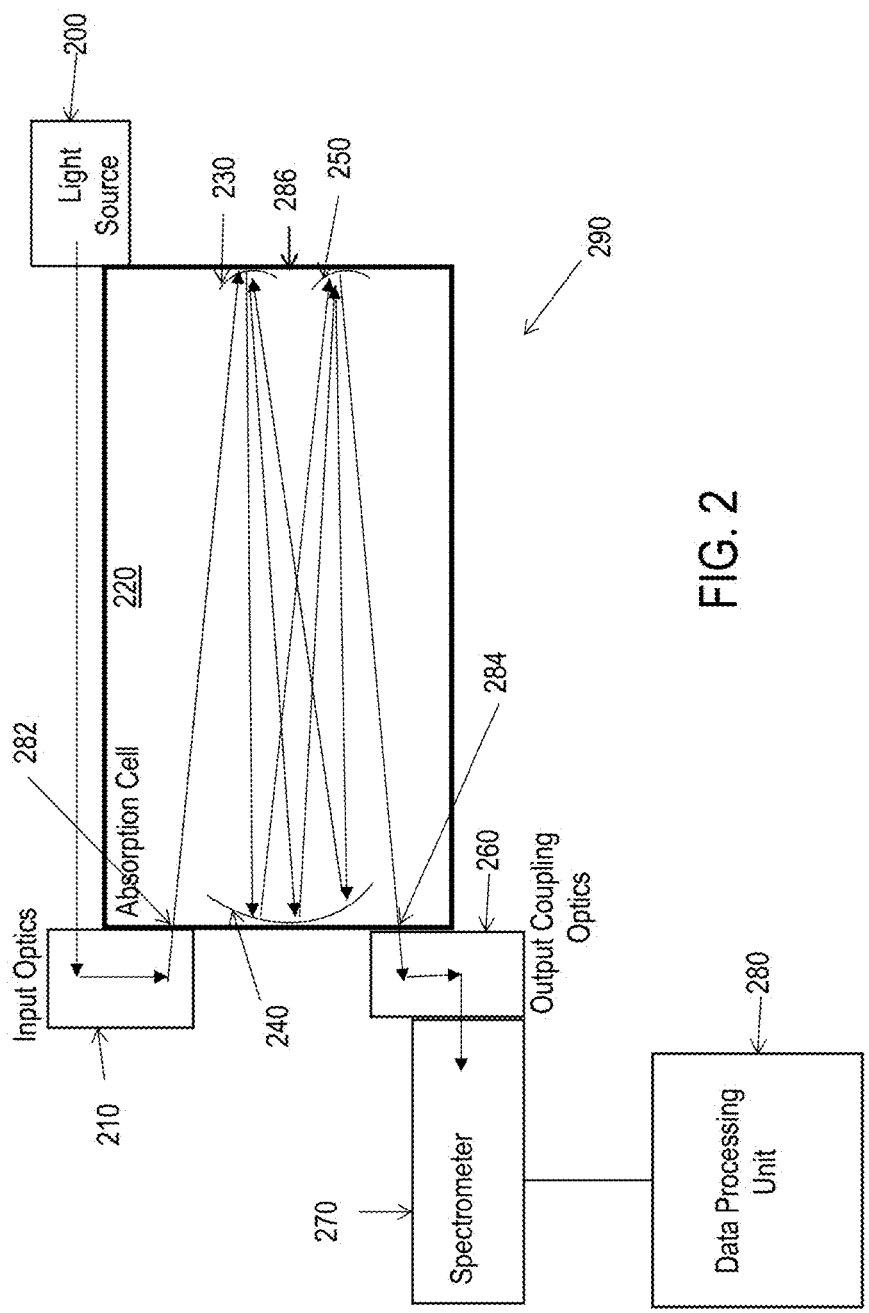
FIG. 2 depicts a representation of an example gas detecting apparatus that uses a multi-pass absorption cell.
Figure 4:
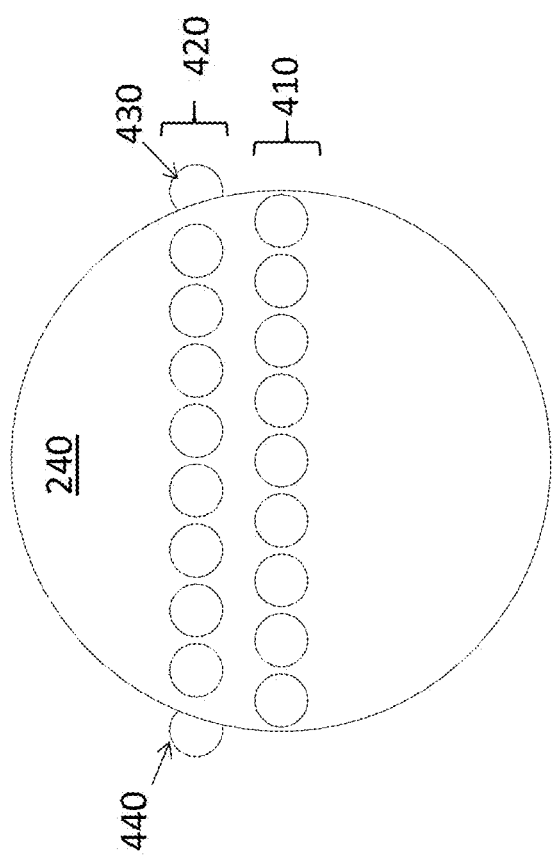
FIG. 4 depicts an arrangement of optical spots on a main mirror of the apparatus shown in FIG. 2.
Figure 5:
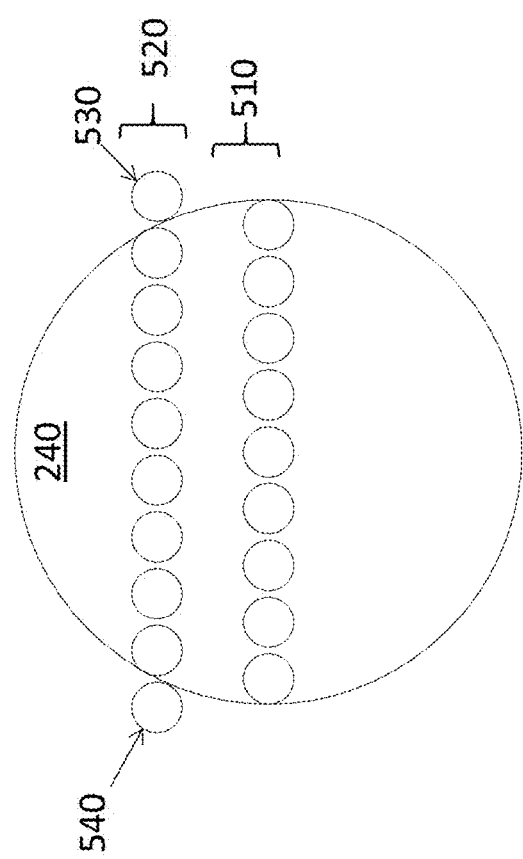
FIG. 5 depicts another arrangement of optical spots on a main mirror of the apparatus shown in FIG. 2.

FIG. 2 depicts a representation of an example gas detecting apparatus 290 that uses a multi-pass absorption cell 220. The gas detecting apparatus includes a light source 200, input optics 210, an absorption cell 220, output coupling optics 260, a spectrometer 270, and a data processing unit 280. In particular, the absorption cell 220 includes three parabolic mirrors: a large mirror 240 and two smaller mirrors 230 and 250. Light enters the cell 220 through an input port 282 and is reflected at a spot on the main mirror 240, then strikes one of the smaller mirrors 230 and 250 at the opposite end of the cell 220 and is returned to be reflected again at yet another spot on the main mirror 240. Light may be reflected back and forth multiple times where each subsequent reflection spot may be aligned on a single axis of the main mirror 240 with a fixed separation. As the number of paths increases, so may the size of the cell 220. In some instances, the size may have to increase in both height and width because the parabolic mirrors are circular in shape. A cell that accommodates a large number of passes of the light between the main mirror 240 and the smaller mirrors 230 and 250 may become quite large and bulky. However, by tilting the small mirrors 230 and 250 relative to the large mirror, allows projecting two rows of reflection spots on the large mirror 240 (as shown in FIG. 4 and FIG. 5). With such alignment of the mirrors, the spot-to-spot spacing can be reduced by half the distance in a standard White cell. For a given number of paths, this approach allows the use of mirror sizes that are slightly more than ¼ the mirror sizes used in the original White cell, yielding a significant reduction in the size of the absorption cell relative to the original White cell design. As a result, the absorption cell 220 is significantly smaller and lighter weight, thereby improving its portability.

In some White cells, the light both enters and exits the cell from the same end. This can cause an issue in that the light source is typically positioned close to the spectrometer. The heating from the light source can thus interfere with the accuracy of the readings from the spectrometer. On the other hand, in the apparatus shown in FIG. 2, input optics 210 including a prism and lensing arrangement and located at the entrance of the absorption cell 220. The light is then directed to an opposite end of the cell 220 and into a spectrometer 270 via an output port 284. Therefore, the spectrometer 270 may be isolated more easily from the heat of the light source 200, thus improving the accuracy and reliability of the apparatus. Further isolation may be realized by using a fiber optic light pipe to direct the light from the light source into the cell, giving the designer the ability to position the light source virtually anywhere.

In UV spectroscopy, a light source such as a Xenon or Deuterium bulb is typically used. These can get very hot, require a lot of power, and have a limited life. A UV Light Emitting Diode (LED) or laser may be used, but the spectral content of these tends to be too narrow and not uniform enough to perform good spectroscopy. A UV LED or laser in combination with a fluorescence agent may produce a simulated white light source, and this may be used as an alternate light source. Combining a plurality of UV LEDs or lasers, each operating at a slightly different wavelength, may generate a broader, more uniform spectrum and may therefore create a suitable light source 200 with much lower power consumption and higher reliability. Infrared spectroscopy may also be possible with a similar arrangement of a plurality of infrared LEDs. If each of the plurality of LEDs is fabricated on the same wafer, die, or chip, then their amplitude characteristics may track over temperature and aging and the relative spectral characteristics of the light may remain constant. This may provide a significant advantage in size, weight, power and robustness.

Further improvements may be made by removing sections of the mirrors that are not being used. If, for example, the reflection spots are arranged as in FIG. 4 or FIG. 5, the main mirror may have unused surface both above and below the area being used for reflection. These unused sections of mirror 240 may be removed, thus allowing a decrease the size of the cell 220 along at least one dimension. Further, the mirror 240 may no longer be circular in shape. For example, the mirror 240 can be shaped and sized to have a perimeter that include only that area over which the rows of light are incident. In some such implementations, the mirror 240 may have an elongated shape.

Other reflection spot arrangements may also be considered. The spots may be arranged to fall radially around the center of the main mirror 240. This may further increase the packing density of the spots on the main mirror, thus allowing a further decrease in the size of the main mirror 240. Additionally, a reflection spot may be used more than once, as long as the angle of incidence is different for each use. Again, this may allow for more paths to exist in a given volume. This can be achieved using precise mirror alignment.

In some instances, environmental effects from expansion and contraction of the apparatus can cause the mirrors to go out of alignment. Further, shock and vibration during transportation can also be an issue. To compensate for these, tiny electromechanical or microelectromechanical systems (MEMS) actuators may be placed to adjust mirror alignment automatically so that the mirrors may be in the optimum configuration and the instrument may be robust.

Dynamic range, or the ability to detect small amounts of gas concentration with high sensitivity as well as being able to detect large concentrations, is another aspect of systems utilizing a multi-pass cell. As the number of times light passes through the cell increases, the light intensity decreases but the spectral absorption increases. Thus, one can detect smaller concentrations but with higher noise. As the gas concentration increases, a smaller optical path length for detection is sufficient. A smaller path length yields more light intensity and enables higher concentrations to be measured by avoiding saturation. By providing MEMS actuators to make adjustments to mirror alignment or shape, we may modify the number of paths within the cell and thus make the instrument more or less sensitive based on the expected range of gas concentrations. In one or more embodiments, at least one of the mirrors 230, 240, and 250 may be formed using a several smaller mirrors, where the positions of one or more of the constituent mirrors can be altered using MEMS actuators. In some such implementations, the overall shape of the mirrors 230, 240, and 250 can be altered by altering the positions of the respective constituent smaller mirrors. In some other embodiments, at least one of the mirrors 230, 240, and 250 can be formed over a flexible material (one or more of plastic, rubber, and/or metal) whose shape can be changed using actuators such as, for example, MEMS actuators.

The amount of light entering into the spectrometer 270 may be controlled by decreasing a size of an opening or aperture, referred to as the slit size. This may be done dynamically or at measurement time to prevent too much light from entering into the instrument and thus saturating the detectors. Slit size may be controlled by using a simple sliding door or a mechanical iris.

Environmental contamination of the cell 220 itself can occur when the metals are exposed to ammonia or other "sticky" gases. The residual "sticky" gas may remain within the cell 220 for extended periods of time, thus contaminating the equipment. Adding a coating such as fluorocarbon on the metal parts may be used to prevent the absorption of these "sticky" gases and thus may allow the instrument to continue to make accurate measurements. A cooling element such as a Thermal Electric Cooler (TEC) may be used to cool the spectrometer 270 to improve sensitivity; however, cooling the unit below the point of condensation may cause the unit to fog and lose sensitivity. By measuring the temperature and humidity in the environment, the unit may then adjust the operating temperature of the spectrometer 270 to just above the point at which fogging can occur and thus may provide the optimum sensitivity. To achieve this, the apparatus can include temperature and humidity detectors for detecting the temperature and humidity in or around the spectrometer 270.

It is desirable to have a mobile gas detection unit that can identify various types of gases and measure their concentration levels. This is typically done using signature analysis, by matching a detected spectral absorption signature with known signatures of the various gasses. The amount of absorption is proportional to a concentration of a gas. However, if multiple gases are present at various concentration levels, the absorption spectrum becomes very complex. Various well known algorithms exist to separate or de-convolve the information and estimate the various constituents and their corresponding concentrations. This can be a very computationally intensive process and the signature libraries can grow considerably with the various constituents the instrument might be called upon to identify. Network or cloud connectivity to a mobile device may be provided to enable the user to upload the raw spectrometer information to a much larger computing and storage platform (cloud computing, such as, for example, cloud 108 shown in FIG. 1B) with an extensive data base of signatures such that a more complete analysis can be provided in the field. Combining this with a less extensive local analysis capability may give end users the option of providing both a rapid assessment of what is being measured as well as a much more thorough analysis if required. Data connectivity to the cloud may be provided through various mechanisms such as, but not limited to, Bluetooth, Cellular, WiFi, and direct wired Ethernet.

After the data from the initial sampling has been processed and analyzed by matching it to particular known species signatures, there might be residual information left in the data set. This residual information is likely from additional species, and either the signatures of those species were not available to the unit or the unit may not have been calibrated to provide an accurate measurement of concentrations for these species. Therefore, the system may be able to detect that other species exist and may inform the user that, without a more comprehensive reading or a more comprehensive database, the unit may need to be recalibrated for these different species and a new signature database and calibration tables may need to be added to the unit's memory. This may be done either at the factory or with cloud connectivity at the measurement site.

In one or more embodiments, the light source 200 can include a Xenon or Deuterium UV light source. The light source 200 emits a light beam down the length of the multipass absorption cell 220 to the input optical coupler 210, which may then direct the light into the cell 220. In cell 220, the light may be reflected between the parabolic mirrors 230, 240, and 250 several times until it exits the cell 220 into the output coupling optics 260. The output coupling optics 260 then direct the light into the spectrometer 270. The spectrometer 270 may have hundreds or thousands of detection channels (for example about 1000 to about 2500 detection channels) with several additional dark channels for calibration purposes. The spectrometer 270 is coupled to a data processing unit 280 through a computer interface, such as, for example, a Universal Serial Bus (USB) interface, a firewire interface, a wired or wireless network interface, and other serial or non-serial interfaces. The data read from the spectrometer 270 may be processed, an estimate of the constituents and their concentrations of the sample within the cell 220 may be estimated, and the information may be provided to the user.

Figure 3:
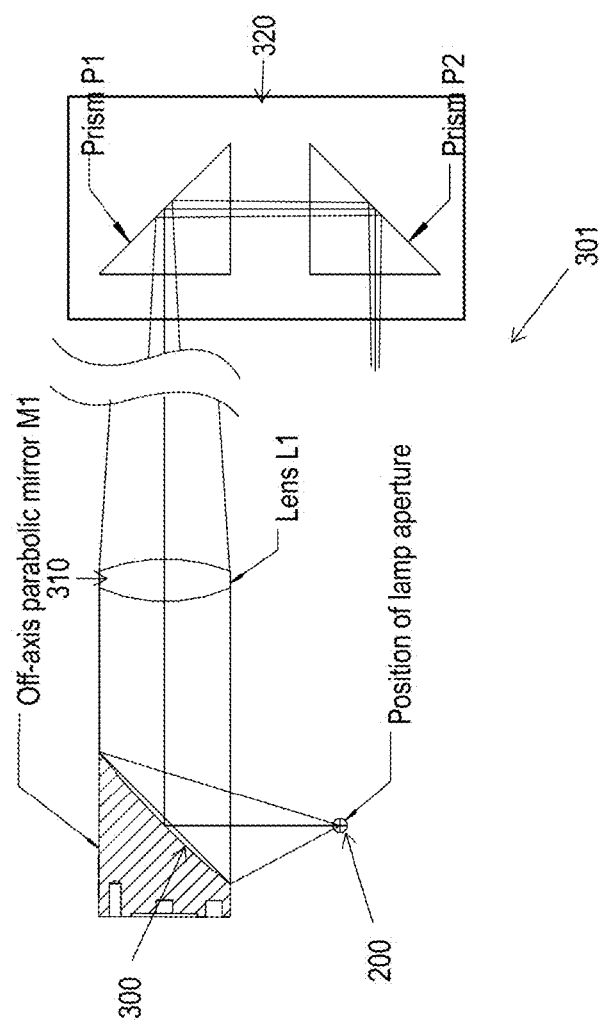
FIG. 3 depicts an example representation of input optics shown in FIG. 2.

FIG. 3 depicts an example representation 301 of the input optics 3 shown in FIG. 2. The input optics 301 include an off-axis parabolic mirror 300, a lens arrangement 310, and a prismatic periscope 320. Light emitting from the light source, such as the light source 200 shown in FIG. 2, may reflect off of an off-axis parabolic mirror 300 and may pass through an air-spaced achromatic doublet lens arrangement 310 to reduce chromatic aberrations. The light may then pass into prismatic periscope 320, where it may then enter the multi-pass cell 220.

In one or more embodiments, an emitting aperture of the light source 200 can be about 0.25 mm to about 0.1 mm, or about 0.5 mm. The aperture can be positioned at about a reflected focal point of the parabolic mirror 300. The parabolic mirror 300 converts the size of the emitting aperture of the lamp into beam of light having a range of angles $\theta = x/f$ where x is the lamp aperture and f is the reflected focal length of the parabolic mirror 300.

In one or more embodiments, the parabolic mirror 300 can be implemented using a Thorlabs UV-enhanced off-axis parabolic mirror. In one or more embodiments, the parabolic mirror 300 can have an aperture of about 0.5 inches to about 1.5 inches or about 1 inch (25.4 mm). In one or more embodiments, the reflected focal length of the parabolic mirror 300 can be about 1 inch to about 3 inches or about 2 inches (50.8 mm).

In one or more embodiments, a numerical aperture (NA), which characterizes the range of angles over which a system can accept or emit light, can be about 0.1 to about 0.5 or about 0.25. In one or more embodiments, the NA of the lamp aperture can be about 0.2 to about 0.6 or about 0.34 in the plane shown in FIG. 3, and about 0.05 to about 0.25 or about 0.17 in a plane orthogonal to the one shown in FIG. 3. In one or more embodiments, about $(0.25/0.34)^2 = 0.54$ of the light emitted by the lamp aperture is collected by the parabolic mirror 300 in the plane shown in FIG. 3 and all of the light emitted by the lamp aperture in the plane orthogonal to the plane shown in FIG. 3 is collected by the parabolic mirror 300. In one or more embodiments, 75% of the light emitted through the lamp aperture is collected by the parabolic mirror 300.

In one or more embodiments, the lens assembly 310 can have an aperture of about 10 mm to about 40 mm or about 25 mm. In one or more embodiments, the lens assembly 310 can have a focal length of about 400 mm to about 800 mm or about 600 mm. The combination of the off-axis parabolic mirror 300 and the lens 310 forms an optical system with magnification M given by the ratio of their respective focal lengths. That is, M=600/50.8=11.8 and forms an image of the emitting aperture of the lamp having a magnified size of about 6 mm in diameter. In one or more embodiments, this diameter represents the NA of the lens assembly 310, and can match the NA of the absorption cell 220. The prismatic periscope 320 can be arranged to direct the light emitted by the lens assembly Once the light enters into multi-pass cell 220, it may be reflected back and forth and may create various spots on mirror 240. One example arrangement of the spots is illustrated in FIG. 4. Two rows of spots may be formed: row 410, which may fall along the horizontal axis, or diameter, of mirror 240, and row 420, which may be parallel but off-axis. There may be two additional spots 430 and 440, which represent the positions of the input light beam 430 and the output light beam 440. Note how these are shown as clipped in FIG. 4. This represents a loss of light intensity that may be undesirable. In one or more embodiments, such as the one shown in FIG. 5, the off-axis row 520 may be further above the horizontal axis row 510 when projected on mirror 240. In this embodiment, the input light beam 540 and the output light beam 530 are no longer clipped and the full amount of light may pass, thus improving the sensitivity of the system.

Figure 6A:
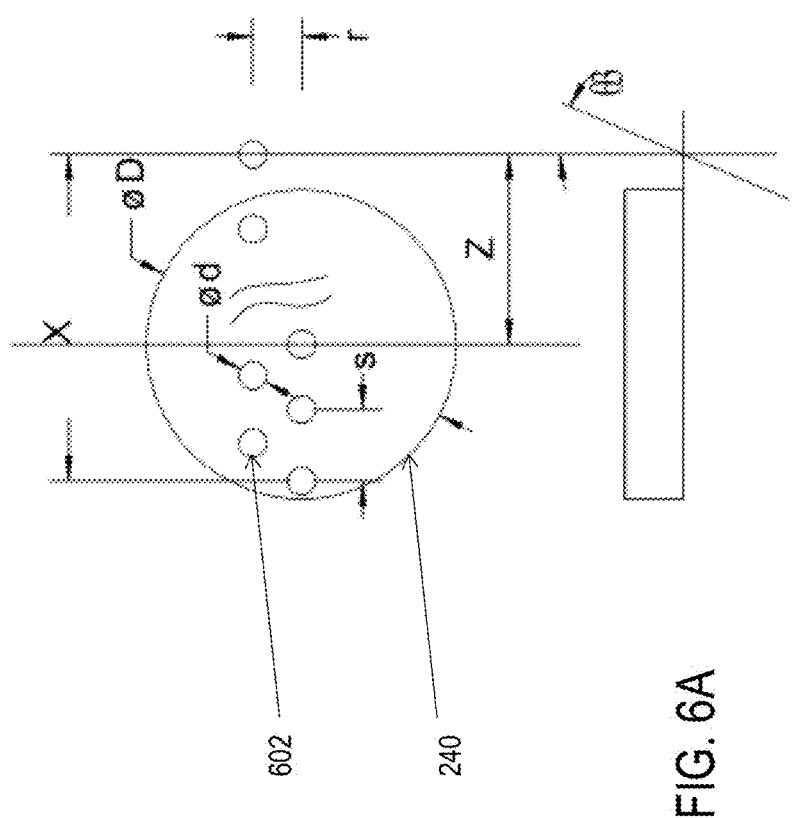
FIG. 6A shows an example representation of light spots on a main mirror of the apparatus shown in FIG. 2.

FIG. 6A shows an example representation of light spots on a main mirror 240. FIG. 6A shows two rows of optical spots 602 formed on the main mirror 240. The spot spacing is denoted by s, the spot diameter is denoted by d, the number of passes is denoted by P, and the main mirror diameter is denoted by D, the row spacing is denoted by r, and an input offset (distance between the input port 282 and the center of curvature of the main mirror 240) is denoted by Z, and its angle is denoted by $\theta_3$.

The number of spots that will fit along the bottom row is related to D, d, and s as described below in Equations (1) and (2):

$$D = \left(\frac{P}{4} - 1\right) \cdot s + d \quad (1)$$

$$s = \frac{D - d}{\frac{P}{4} - 1} \quad (2)$$

By inspection, the distance X, between the location where the input beam enters the cell at port 282 and the location of the spot formed by the first light beam reflected from the first small mirror 230, can be described by Equation (3) below:

$$X = \left(\frac{P}{4} - 1\right) \cdot s + \left(\frac{s}{2}\right) \quad (3)$$

Substituting s from Equation (2) into Equation (3) results in Equations (4) and (5) below:

$$X = D - d + \frac{1}{2}\left(\frac{D - d}{\frac{P}{4} - 1}\right) \quad (4)$$

$$X = (D - d) \cdot \left(\frac{\frac{P}{2} - 1}{2\left(\frac{P}{4} - 1\right)}\right) \quad (5)$$

Figure 6B:
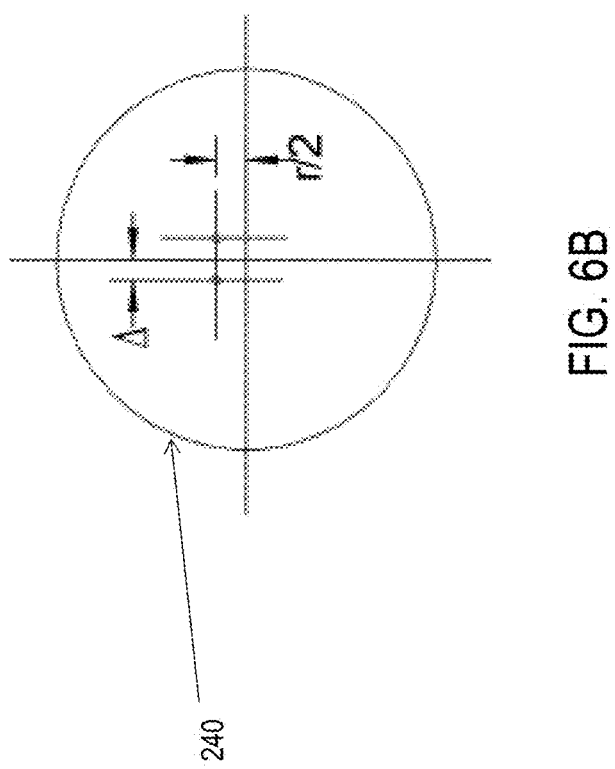
FIG. 6B shows an example representation of positions of small mirrors' center of curvatures in relation to a main mirror.

FIG. 6B shows an example representation of positions of small mirrors (230 and 250) center of curvatures on the main mirror 240. In particular, distance of the center of curvature of the small mirrors from the center or curvature of the main mirror 240 is denoted by Δ, which can be described by Equations (6) and (7) below:

$$\Delta = (D - d) \cdot \left(\frac{\frac{P}{2} - 1}{4\left(\frac{P}{4} - 1\right)} - \frac{1}{2}\right) \quad (6)$$

$$\Delta = \frac{(D - d)}{(P - 4)} \quad (7)$$

As an alternative to deriving the Equations (6) and (7) above, by inspection it can be seen that the input to the abruption cell 220 is displaced with respect to the end spot on the bottom row by s/2. As the angle of incidence and reflection of a mirror are the same, the center of curvature of the small mirror (230 or 250) is displaced from the center of curvature of the main mirror 240 by s/4, which similar to the result of Equation (7). In one or more embodiments, as an example, for an arrangement of the mirrors where P=36 (i.e., 36 pass cell), d=5 mm, and D=50 mm, we get Δ=(50−5)/(36−4)=1.41 mm. Thus, the center of curvature spacing of the small mirror with respect to the center of curvature of the main mirror 240 is about 2.82 mm. This about half the spot size of about 5.63 mm.

Figure 6C:
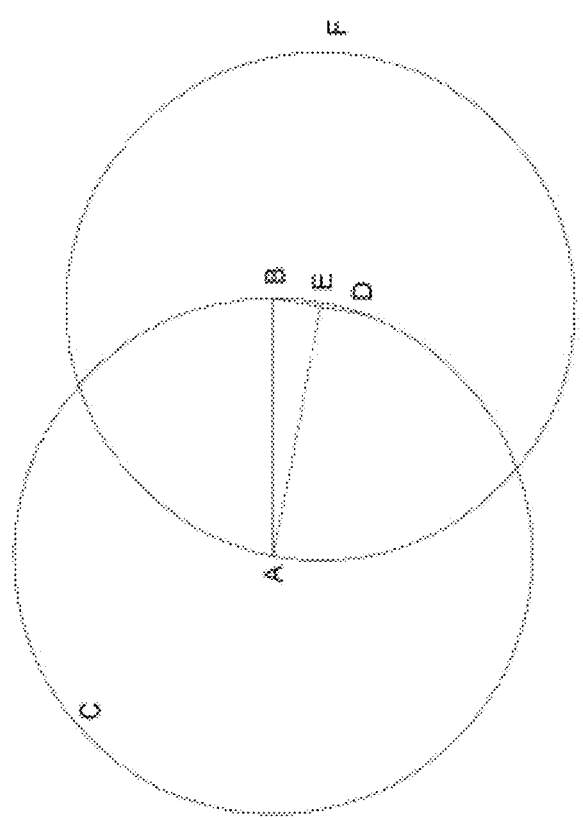
FIG. 6C depicts an example representation of spacing between rows of optical spots on a main mirror of the apparatus shown in FIG. 2.

FIG. 6C depicts an example representation of spacing between rows of spots. Row spacing geometry can be specified using the following steps: (1) drawing a horizontal line AB proportional to a distance L between a main mirror located at point B and a small mirror located at point A; (2) drawing a circle C centered at A and having a radius equal to L; (3) drawing a segment BD equal in length to the desired row spacing; (4) drawing a point E halfway between B and D; and (5) drawing a circle F centered at E and with radius equal to the distance between points A and B. The curve of the circle F represents the curvature of the small mirror. This shows that a tilt axis of the large mirror, specified by the angle BAD is twice the tilt angle of the small mirror specified by angle BAE.

In one or more embodiments, the line AB can represent an input and output axis, and point D represents a position of row of spots along a diameter of the large mirror.

FIG. 6D depicts mirror overlays on the representation depicted in FIG. 6C. A tilt angle $\theta_2$ (specified by the angle BAE) is equal to half the row spacing (r) divided by the mirror spacing L (specified by the length of the segment AB). The tilt angle can be expressed by Equation (8) below:

$$\theta_2 = \frac{r}{2L} \quad (8)$$

In one or more embodiments, for example, where L=500 mm, the tilt angle $\theta_2$ for a row spacing of about 8 mm is equal to about 8 m-radians. As the tilt angle of the large mirror is about twice the tilt angle of the small mirror, the tilt angle of the large mirror would be equal to 16 m-radians. In this manner, the tilt angles of the small mirrors 230 and 250 and the tilt angle of the large mirror 240 can be determined.

The light enters the absorption cell 220 form the input port 282 at an angle of incidence, and leaves the absorption cell 220 from the output port at another angle, that is substantially equal to the angle of incidence. This is because the absorption cell 220 is arranged symmetrically about an axis that joins the centerline of the main mirror 240 to a center 286 of small mirrors 230 and 250. The small mirrors 230 and 250 are positioned one either side of the center 286 and at the same distance from the center 286. Referring to FIG. 6A, the beam positions at input and output are spaced by s/2 from the first and last internal spots. In one or more embodiments, the input port 282 and the output port 284 are equally spaced from the centerline of the large mirror 240. The distance of the input port 282 and the output port 284 can be specified by Equation (9) below:

$$Z = \left(\frac{P}{P-4}\right)\frac{(D-d)}{2} \quad (8)$$

Thus, for example, in an absorption cell configured for 36 passes (i.e., P=36), with D=50 mm, and d=5 mm, the value of Z=25.3 mm. An angle $\theta_3$ subtended by the input light ray from the input port 282 with respect to the small mirror center 286. In some embodiments, where the distance between the main mirror 240 and the center 286 is about 500 mm, the angle $\theta_3$ can be determined to be about 23.2 m-radians (or 1.33 degrees).

Figure 6E:
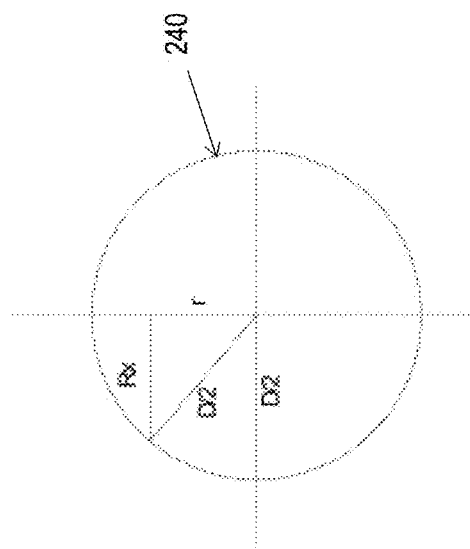
FIG. 6E shows an example representation of a main mirror for determining clipping of light beams.

As discussed above one of the challenges in using a multi-pass absorption cell 220 is a loss of intensity of light due to light beams clipping the main mirror 104. Referring again to FIG. 4 two rows 220 and 210 of spots are shown on the main mirror 240. The spots 230 and 240 in the row 220 are clipped at the edge of the main mirror 240. FIG. 6E shows an example representation of the main mirror 104 for determining the clipping of light beams. In particular, radius r denotes the distance between centers of two rows of spots (such as the rows 210 and 220 shown in FIG. 4), D denotes the diameter of the main mirror 240 and Rx denotes the distance of the edge of the mirror 240 from the centerline of the mirror 240. Based on the geometry disclosed, the Rx×2= (D/2+r)/(D/2−r). Thus, for a diameter D=50 mm, and distance r between the rows being 8 mm, Rx=23.7 mm. For a 20 pass design, discussed above, Z=27.5 mm. As Rx=23.7 mm, the centerline of the clipped spots lies 27.5−23.7=3.8 mm from the edge of the mirror 240. Since the spot diameter is about 6 mm, the clipping can be avoided. Generally, the distance r between the rows can be selected such that the resulting value of Rx is sufficiently large with respect to Z to avoid clipping. This is shown in FIG. 5, where the spots 330 and 340 do not clip at the edge of the main mirror 240.

In one or more embodiments, the alignments of the small mirrors 230 and 15 and the large mirror 240 can be adjusted based on the desired number of passes, the desired number of passes of the input light beam within the absorption cell 220 before it is analyzed by the spectrometer 270. For example, Equation (7), discussed above, can be used to determine the distance (denoted by Δ) of the center of curvature of the small mirrors from the center or curvature of the main mirror 240. In one or more embodiments, the following look-up Table 1 can be used to determine Δ for various values of the number of passes:

TABLE 1

| Number of passes | Small mirror CC Δ (mm) |
|---|---|
| 8 | 11.00 |
| 12 | 5.50 |
| 16 | 3.67 |
| 20 | 2.75 |
| 24 | 2.20 |
| 28 | 1.83 |
| 32 | 1.57 |
| 36 | 1.38 |
| 40 | 1.22 |

Subsequently, an angle of the small mirrors needed to provide the increase or decrease in the number of passes selected from Table 1 can be selected using the look-up Table 2 below:

TABLE 2

| Number of passes | Angle change to increase passes by 4 (mrads) | Between passes and passes |
|---|---|---|
| 8 | | |
| 12 | 11.00 | 12 to 8 |
| 16 | 3.67 | 16 to 12 |
| 20 | 1.83 | 20 to 16 |
| 24 | 1.10 | 24 to 20 |
| 28 | 0.73 | 28 to 24 |
| 32 | 0.52 | 32 to 28 |
| 36 | 0.39 | 36 to 32 |
| 40 | 0.31 | 40 to 36 |

As mentioned above, the alignment of the small mirrors 230 and 250 can be adjusted using actuators such as MEMS actuators. In one or more embodiments, the actuators can be selected based on the accuracy needed to adjust the angle of the mirrors. For example, the following Table 3 provides adjustment angle accuracy needed with a Standa mount.

TABLE 3

| Number of passes | Between Passes and passes | Passes angle (column 2 above) × 0.2 | Adjustment angle accuracy of Standa mount (degrees turn) |
|---|---|---|---|
| 8 | | | |
| 12 | 12 to 8 | 2.200 | 90.76 |
| 16 | 16 to 12 | 0.733 | 30.25 |
| 20 | 20 to 16 | 0.367 | 15.13 |
| 24 | 24 to 20 | 0.220 | 9.08 |
| 28 | 28 to 24 | 0.147 | 6.05 |
| 32 | 32 to 28 | 0.105 | 4.32 |
| 36 | 36 to 32 | 0.079 | 3.24 |
| 40 | 40 to 36 | 0.061 | 2.52 |

As shown in Table 3, for a 24 pass absorption cell 220, the adjustment accuracy of the Standa mount is about +/−10 degrees turn. Further, the adjustment accuracy increases as the number of turns squared.

Figure 7:
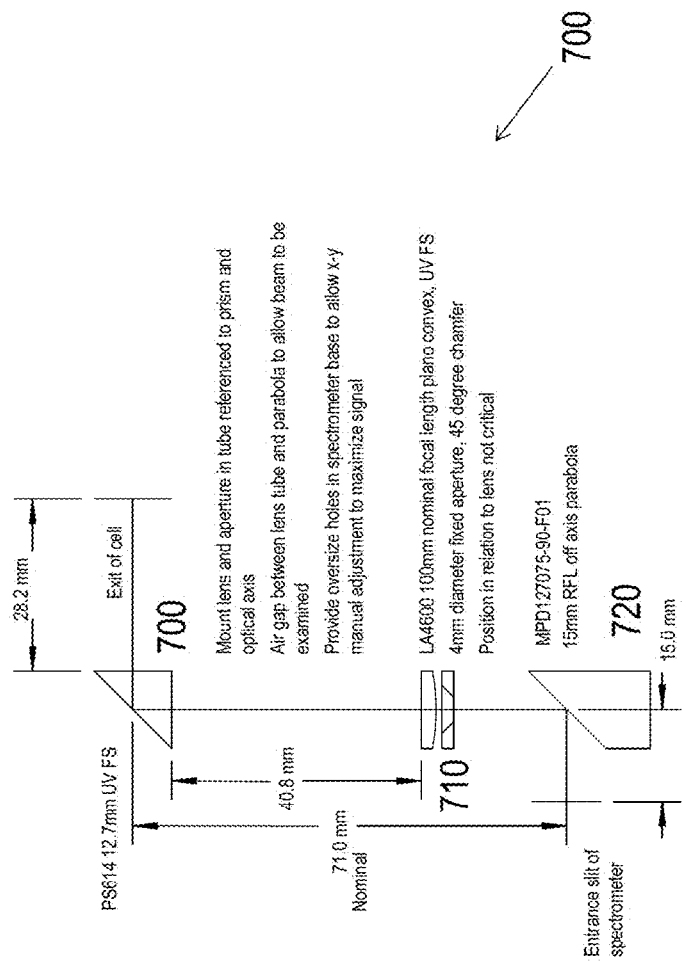
FIG. 7 depicts a representation of an example of an output coupling optics of an apparatus shown in FIG. 2.

FIG. 7 depicts a representation of an example of output coupling optics 750. In particular, the output coupling optics 750 can be used to implement the output coupling optics 260 shown in FIG. 2. The output coupling optics 700 include a first prism 700, a lens 710 and a parabolic mirror 720. As the light exits the multi-pass cell 220 it enters into output optical unit 260 where the light passes through the fused silica prism 700 and then through lens 710 where it may be focused and reflected off the parabolic mirror 720 and then directed into the opening slit of the spectrometer 270. In one or more embodiments, the ratio of the focal length of the parabolic mirror to the focal length of the lens 710 can be selected such that the spot size of the beam of light exiting the absorption cell 220 is increased or decreased to match the size of the entrance slit of the spectrometer 270. For example, for a slit size of about 1 mm, and a spot size of about 6 mm exiting the absorption cell 220, the ratio can be selected to be about 0.15 such that the spot size is reduced to about 0.9 mm. It should be noted that the dimensions of the output coupling optics 700 shown in FIG. 7 only depict non-limiting example dimensions.

Metal parts such as metal walls contained within the multi-pass cell 220 may have a fluorocarbon coating to prevent absorption of ammonia or other similar species. Without this coating, the presence of ammonia inside the cell can pollute the metal walls of the cell such that the presence of ammonia is always detected whether or not it is present in the sample.

In one or more embodiments, the spectrometer 270 may be capable of 2048 measurement points and over-samples data at 50 samples per second. The data processing unit 280 may perform various signal processing algorithms to remove noise from the data and may downsample the data, for example, to one sample per second. This may improve the overall quality and sensitivity of the measurement. In one or more embodiments, the spectrometer 270 may cover a range of 190 nanometers to 350 nanometers, but many of the species of interest may not require this full range. The signal processing algorithms may be designed to be able to reduce selectively the measurement range to speed up the processing of the measurement data. This range may be increased or decreased during the course of a measurement cycle as the species entering the system change.

Figure 8:
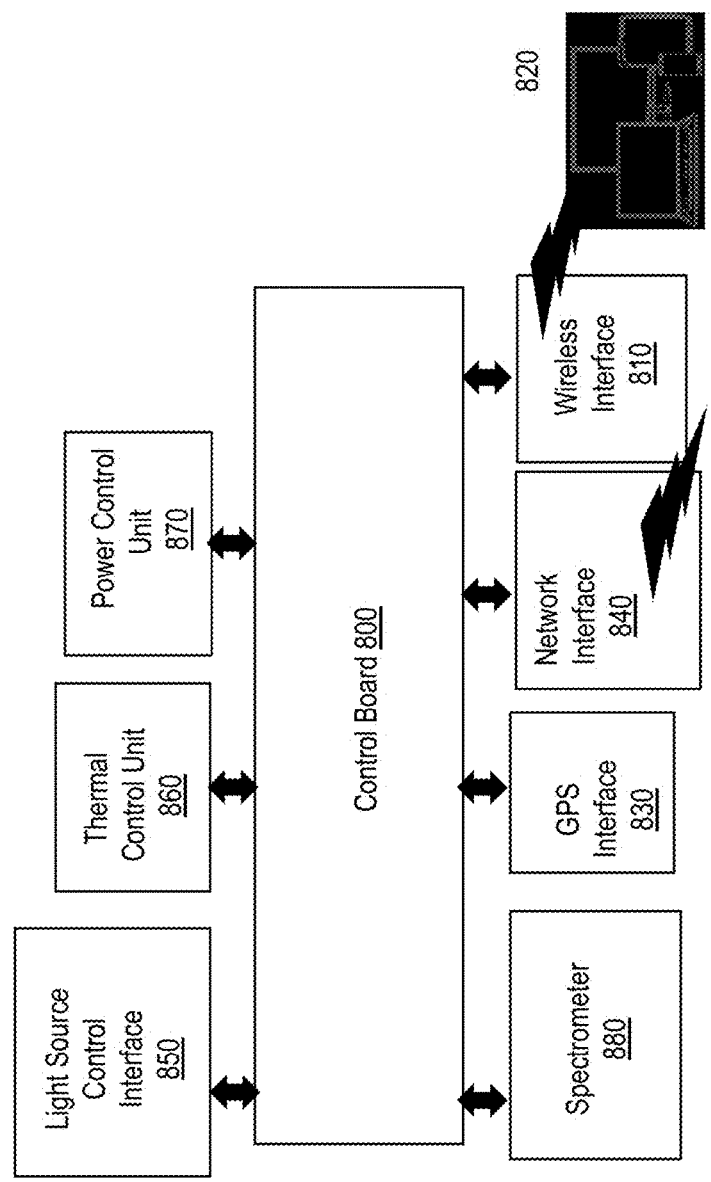
FIG. 8 shows a block diagram representation of an example gas and vapor detection system.

FIG. 8 shows a block diagram representation of a gas and vapor detection system. The main computational and control board 800 may consist of a typical CPU board, which anyone skilled in the art will recognize. Standard peripheral interfaces may be provided to communicate with and control the various devices in the system. Wireless interface 810 may be provided to communicate with the operator interface device 820, which may be any handheld or mobile device with a corresponding wireless interface. The system may also contain a Global Positioning System (GPS) interface 830, which may be used to record the exact position where a measurement is made and the exact time of day. Interface 840 may be a wireless cellular data interface that may be used for remote or mobile cloud connectivity. Light source control interface 850 may control the light source used to illuminate the sample. Thermal control of the various components in the system may be accomplished with thermal control unit 860, which may control a plurality of temperature compensation devices, fans, Thermal Electric Coolers (TEC), and temperature measurement devices. To facilitate portability, the unit may be battery powered. Power control unit 870 may monitor available energy within the battery system and may also provide battery protection and may control the charging of the Lithium Ion (Li-ion) battery cells for safety. Spectrometer 680 may interface with controller 800 through a Universal Serial Bus (USB) interface.

As shown in FIG. 9, electronics unit 910 may be connected to user interface 960 and spectrometer and optics system 900. The electronics unit may also contain wireless interface 920, which may provide connectivity to the cloud 930. In one or more embodiment, the cloud 930 can be implemented using the cloud 180 discussed above in relation to FIGS. 1A-1D. Within the cloud there may be additional processing, diagnostics, and/or life cycle management capabilities contained in the cloud computational unit 940 and cloud storage unit 950. Cloud storage unit 950 may contain a database which includes the calibration information for the portable unit, it may record the location provided by GPS unit 830 of data samples measured by spectrometer 880. Maintenance to firmware for control board 800 and the local signature database may be managed by cloud computational unit 940. Information for the operator may also be provided through the cloud connection that may include but is not limited to where specifically to take samples and how to position the unit for best detection.

The invention claimed is:

1. A system for identifying species in a fluid, the system comprising:
   a light source generating a detection light;
   an input optical coupling unit configured to receive the detection light at a first angle and output the detection light at a second angle;
   a multi-pass absorption cell containing the fluid having an input port positioned at one end of the cell and an output port positioned at an opposing end of the cell, the cell configured to receive the detection light output by the input optical coupling at the input port, pass the detection light through the fluid, and output the detection light through the output port;
   an output optical coupling unit configured to receive the detection light output by the cell at a third angle and output the detection light at a fourth angle, the output optical coupling unit including a prism, a lens, and an off-axis parabolic mirror positioned in a path of the detection light;
   a spectrometer configured to receive the detection light output by the output optical coupling unit at an entrance slit and generate spectral data related to the detection light, wherein a ratio of the focal length of the parabolic mirror to a focal length of the lens is selected such that a spot size of the detection light output by the output optical coupling unit is less than the entrance slit size; and an electronic unit configured to receive spectral data from the spectrometer and analyze the spectral data.

2. The system of claim 1, wherein the input optical coupling unit includes an air-spaced achromatic doublet lens and a periscope.

3. The system of claim 1, wherein the prism is a fused silica prism, and the lens is a fused silica lens.

4. The system of claim 1, further comprising a temperature controller for controlling the temperature of the spectrometer.

5. A system for identifying species in a fluid, the system comprising:
- a light source generating a detection light;
- a multi-pass absorption cell configured to receive the detection light, pass the detection light through the fluid, and output the detection light through an output port;
- an output optical coupling unit configured to receive the detection light output by the cell at a first angle and output the detection light at a second angle, the output optical coupling unit including a prism, a lens, and an off-axis parabolic mirror positioned in a path of the detection light;
- a spectrometer configured to receive the detection light output by the output optical coupling unit at an entrance slit and generate spectral data related to the detection light, wherein a ratio of the focal length of the parabolic mirror to a focal length of the lens is selected such that a spot size of the detection light output by the output optical coupling unit is less than the entrance slit size; and
- an electronic unit configured to receive and process the spectroscopic data received from the spectrometer, the electronic unit including at least one communication interface to communicate with at least one computational unit and at least one storage unit.

6. The system of claim 5, wherein the communication interface includes a wireless interface.

7. The system of claim 5, wherein the electronic unit is configured to process a portion of the spectral data and communicate another portion of the spectral data to the at least one computational unit over the communication interface.

8. The system of claim 5, wherein the electronic unit is further configured to receive from the at least one computational unit or the at least one storage unit species identification information different from species identification information present at the electronic unit.

* * * * *